United States Patent [19]

Delizo-Madamba

[11] Patent Number: 5,320,531
[45] Date of Patent: Jun. 14, 1994

[54] ABSORBENT FINGER SLEEVE FOR USE IN DENTISTRY OR MEDICINE

[76] Inventor: Peggy A. Delizo-Madamba, 7709 202nd Pl. SW., Edmonds, Wash. 98026

[21] Appl. No.: 7,512

[22] Filed: Jan. 22, 1993

[51] Int. Cl.$^5$ ............................................. A61C 5/14
[52] U.S. Cl. ...................................... 433/136; 15/227
[58] Field of Search ............. 433/136; 128/62 A, 880; 401/7; 604/308, 1, 2, 3; 15/227; 2/21

[56] References Cited

U.S. PATENT DOCUMENTS

| | | | |
|---|---|---|---|
| 2,068,400 | 1/1937 | De Rome | 15/227 |
| 2,318,365 | 5/1943 | Boysen | 15/227 |
| 2,474,535 | 6/1949 | Krannak | 2/21 |
| 3,647,305 | 3/1972 | Baker et al. | 401/7 |
| 3,902,509 | 9/1975 | Tundermann et al. | 15/227 |
| 3,952,867 | 9/1975 | McCord | 401/7 |
| 4,588,400 | 5/1986 | Ring et al. | 604/304 |

Primary Examiner—Cary E. O'Connor
Attorney, Agent, or Firm—Stephen M. Evans; David L. Garrison

[57] ABSTRACT

An absorbent sleeve formed to fit over at least the distal portion of a finger to absorb fluids and remove debris from constrained areas of the body such as canals and cavities, or to apply fluid substances is disclosed. The sleeve has an upper and lower portion which may be of equal length. In a preferred embodiment, the upper and lower portion are of differing lengths with the lower portion having an appendage attached thereto to facilitate safe and convenient removal of the sleeve after use. The sleeve also preferably has a fluid impermeable layer between an external surface of the sleeve and an inserted finger to create a fluid barrier. The sleeve may have a friction enhancing member to prevent unintentional removal of the sleeve during use.

7 Claims, 2 Drawing Sheets

ABSORBENT FINGER SLEEVE FOR USE IN DENTISTRY OR MEDICINE

FIELD OF THE INVENTION

The present invention relates to the field of fluid absorbent accessories for use in the dental field. More particularly the invention is directed to the field of dental applications wherein a sterile and absorbent material is to be inserted into a constrained area or cavity. The invention is equally suited for use in the medical field where similar conditions are encountered, or in the cosmetics field.

BACKGROUND OF THE INVENTION

It is a fact that more and more attention is being focused on preventative health care and more particularly on preventative dental health care. Recently, consumers have been provided with advanced products such as periodontal tipped tooth brushed, plaque reducing mouth rinses, specially formulated tartar control tooth pastes, and magnetically enhanced oral irrigators. The thrust of these products has been to remove residue from teeth to prevent bacteria build-up that has been linked to tooth decay and tooth loss. Moreover, the subject of gum disease has been receiving more and more attention, and consumer products associated with treating conditions of the gums have also been increasing.

There is, however, a noticeable absence of products directed towards the infant and elderly population. This segment of the population can be characterized as those persons who do not have exposed teeth or have lost a significant portion or all of their teeth. Many of these persons are unable to care for themselves. Consequently, the predominant concern for these individuals relates to gum care, care that must often times be rendered by other persons. In these situations, health and care of the gums and surrounding tissue is primary concern.

Unfortunately for these people, most currently avaiable devices are ill suited for their special needs. For example, persons without teeth have little need for periodontal equipped tooth brushes let alone tooth brushes. Nor do they have a need for plaque reducing mouth rinses, tartar control tooth pastes, oral irrigators, dental floss, etc. The principle concern is the removal of food debris and bacteria from the gum and inner lip areas to prevent undesired bacteria buildup which could lead to an elevated risk of gum and bone damage.

In some situations, simply rinsing the mouth will remove much of the debris and bacteria from a person's mouth. However, very small children or mentally and/or physically challenged persons may be incapable of rinsing and expelling a mouth rinsing fluid. But because many persons, including the very young and the physically disabled, are incapable of rinsing, the predominant form of oral hygiene involves assisted physical removal of debris and bacteria.

In the field of assisted oral hygiene, a preferred method used to remove debris and bacteria from the oral cavity has utilized swab type devices. An example of such a device is a sponge for medical, dental or surgical use as is shown in U.S. Pat. No. D. 206,641. These devices can absorb large quantities of fluid. They also keep the hand distant from the fluid source. While these devices can remove debris and bacteria, they are generally awkward and often bulky when used and wasteful when disposed of. Moreover, such devices have limited articulation, an important consideration in the dental field where proper and efficacious cleaning involves considerable probing into pockets and crevices that are not easily accessible when using a rigid device. And perhaps most importantly, these devices provide minimal tactile feedback. Tactile feed back is extremely important when probing or cleaning sensitive areas in the mouth, such as those of infants, the elderly, or any person having inflamed tissue therein.

As a partial response to this need, some individuals in the health and/or dental care profession have taken gauze pads and loosely wrapped them around their finger. The gauze wrapped finger was then inserted into the mouth to remove debris therefrom. After use, the gauze was conveniently disposed of. This method combined the advantages of using an articulated and touch sensitive implement, with the advantages of using a sterile and absorbent media that could be easily disposed of.

However, the gauze over the finger adaptation was not without limitations. The gauze pads would often come loose from the finger. Moreover, fluids from the mouth would often permeate to the finger. Exposure of skin, possibly having an open cut or the like, with mucous or body fluids is presently of great concern in light of potential viral infections such as those caused by the HIV virus, or the like. In addition, removal of the gauze pads, if they didn't become detached during use, would require grasping them—a practice which again exposed the surface of an otherwise unprotected finger to body fluids.

From the foregoing, it is equally clear that the absorption of fluids and removal of debris is not limited to the field of dentistry and oral hygiene. The medical field also has similar needs and problems. Removal of debris from cuts near a bone is often accomplished by grasping a gauze pad by hand or by instrument and probing the injured area. However, often times debris (and bacteria) are forced into the surrounding tissue. A gauze pad held between a finger and thumb is often too large to probe these areas; a gauze pad held by an instrument lacks tactile sensitivity Therefore, a need exists to have an implement that combines the benefits of a gauze wrapped finger with the benefits of a swab type device.

SUMMARY OF THE INVENTION

The present invention comprises a single use, absorbent, disposable finger sleeve for removing debris and bacteria from confined crevices and cavities. Primary uses of the invention comprise dental and medical cleaning, and cosmetic applications. The invention comprises a sterile, absorbent material that is formed to fit over the distal portion of a human finger to provide an appropriate surface with which to explore an oral cavity to remove foreign debris and bacteria, or to explore injured tissue of the body to remove foreign debris, or to remove or apply cosmetic related products. In a preferred embodiment, the sleeve has an upper and lower portion corresponding to the dorsal and palmer surface of a finger. The lower portion is preferably longer than the upper portion or it may have an appendage attached thereto. This appendage, which is preferably a lengthened section of tear resistant material, provides a convenient portion which may be easily grasped to aid in the application or removal of the sleeve. The upper and lower portions may be separate components during manufacture, or the sleeve may be constructed from a unitary piece of material.

A feature of the invention provides for a friction enhancing portion of the sleeve to keep it positively located on the finger during use. In a preferred embodiment, the friction enhancing portion comprises an elastic member or gathered section extending around the circumference of the sleeve. This elastic member constricts around a finger inserted into the sleeve, thereby creating an area of increased friction that resists movement of the sleeve relative to the inserted finger and decreases the likelihood of the sleeve being inadvertently removed during a cleaning procudure.

Another feature of the invention provides for medicated or fluid impregnated absorbent material. In the embodiment characterized by this feature, not only does the sleeve collect and physically remove debris and bacteria, but it may also treat inflamed or infected areas with antibiotics or the like, or chemically neutralize bacteria and other targeted substances. By providing such a sleeve, there is no longer a need to have a separate source of antibiotics, bactericide, or the like. A user need only insert a finger into the sleeve and proceed to clean and medicate or disinfect.

Yet another feature of the invention provides for a fluid impermeable layer, intermediate the absorbent lay and the surface of a finger, thereby forming a fluid barrier. By incorporating such a feature, the portion of the finger inserted into the sleeve is wholly protected from exposure to the absorbed fluid without requiring the use of a separate protective barrier such as a latex glove.

From the foregoing, it should be clear that the present invention provides a convenient, disposable, and efficacious absorbent accessory especially suited for use in sensitive areas of the body or areas that have limited accessibility.

DETAILED DESCRIPTION OF THE INVENTION

Figure 1:
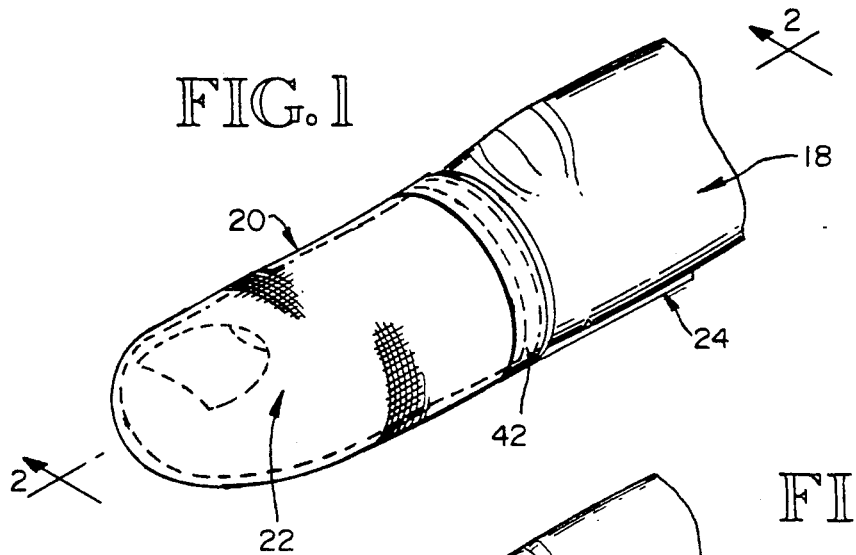
FIG. 1 is a perspective view of a preferred embodiment of the invention with a finger, shown in phantom, inserted therein.
Figure 4:
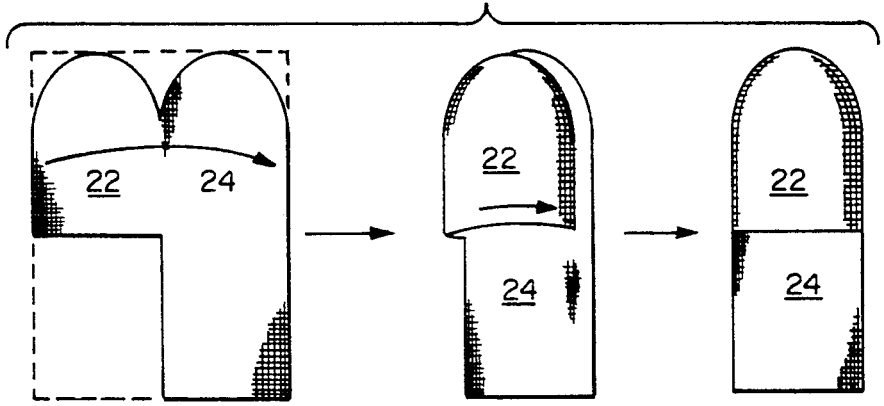
FIG. 4 is a plan view illustrating the steps of forming the sleeve from a single sheet of material, shown by dashed lines, into a preferred embodiment.

Referring then to the several figures wherein like numerals indicated like parts and more specifically to FIG. 1 a perspective view of the invention is shown with an inserted finger 18. Sleeve 20 generally comprises an upper portion 22 and a lower portion 24 that are formed to fit over a finger 18. Upper portion 22 and lower portion 24 may be constructed from a single sheet of absorbent material such as gauze or the like (See FIG. 4), or two such sheets of absorbent material (See, e.g., FIG. 5). Each portion has a major axis which is considered to be parallel to the axis of an inserted finger 18.

Lower portion 24 is preferably axially longer than upper portion 22. By constructing lower portion 24 to be axially longer than upper portion 22, more fluids and debris can be absorbed and collected by sleeve 20 during its use since the palmer area of finger 18 is generally subject to more fluids and debris during exploration of constrained areas or body cavities.

Figure 1A:
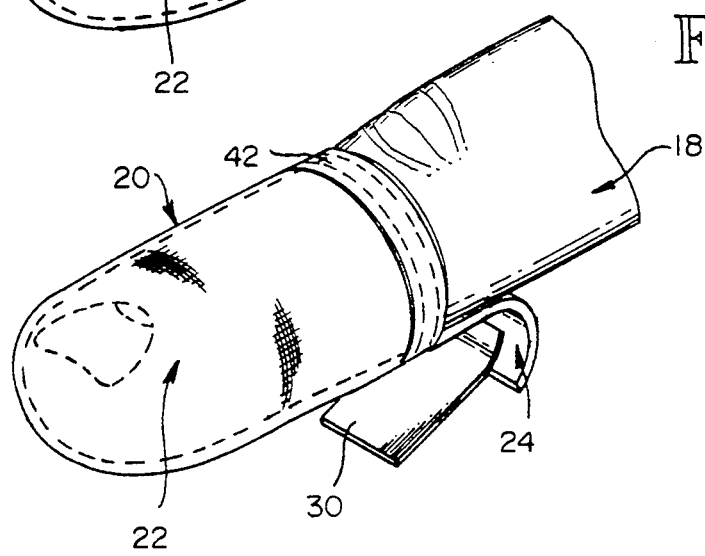
FIG. 1A is similiar to FIG. 1 but illustrates an elongated appendage attached to the lower portion of the sleeve to facilitate the application or removal of the sleeve.

An additional benefit of having lower portion 24 longer than upper portion 22 is that application and removal of sleeve 20 from finger 18 is greatly enhanced. As illustrated in FIG. 1A, lower portion 24 may be pulled back from finger 18 at its proximal end. To enhance this attribute of the invention, appendage 30 may be fixedly attached to the proximal end of lower portion 24 to further lengthen lower portion 24. Moreover, appendage 30 is generally not subject to the fluids and/or debris as is lower portion 24 and upper portion 22 because of its distance from the fingertip. Consequently, appendage 30 provides a suitably uncontaminated grasping surface when removing sleeve 20 form a finger 18. The same rationale holds true when applying sleeve 20 to a finger 18. By only grasping appendage 30 when inserting a finger into sleeve 20, the sterile quality of the absorbent material of sleeve 20 is preserved.

Figure 2:
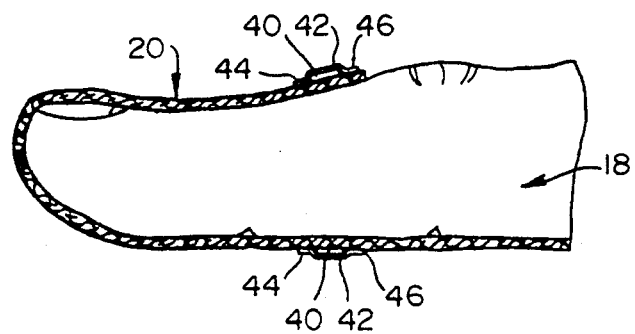
FIG. 2 is a partial cross sectional view taken substantially along the line 2—2 of FIG. 1.
Figure 3:
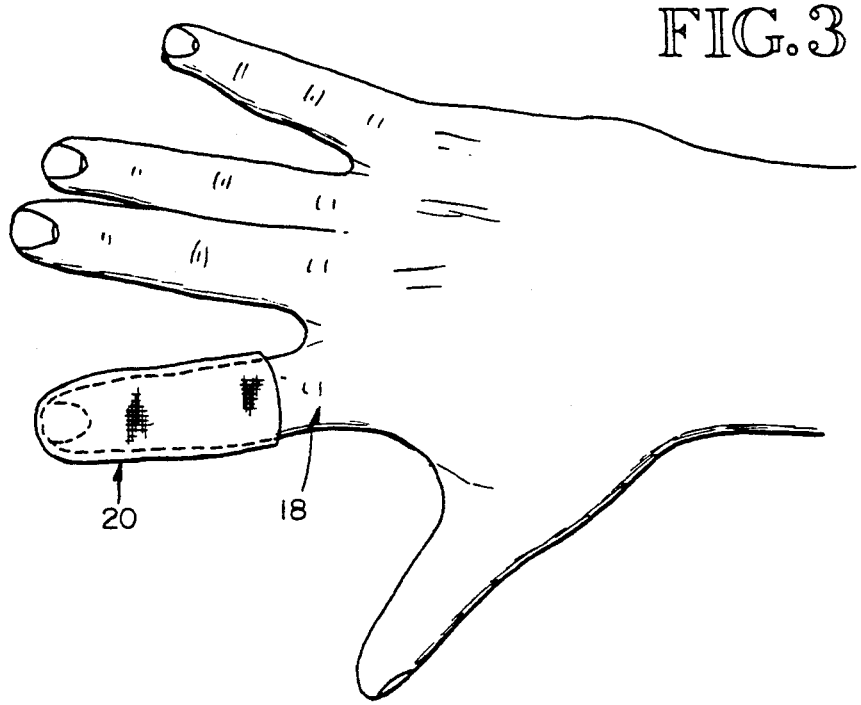
FIG. 3 is a plan view of an alternative embodiment wherein the sleeve substantially envelopes all phalanges of an index finger.

To prevent the premature removal of sleeve 20 from finger 18 that may occur during use, a means to enhance the friction between sleeve 20 and a finger 18 is disclosed. In the preferred embodiment, an elastic member 40 is incorporated into sleeve 20. Elastic member 40, as shown in FIGS. 1, 1A, and 2 is a generally annular band of elastic material, located at or near the exterior surface of sleeve 20 near the proximal end of upper portion 22, which circumferentially extends around sleeve 20. Elastic member 40 may be bonded to sleeve 20 or held proximately thereto by securing means such as enclosing layer 42. As best shown in FIG. 2, enclosing layer 42 positively locates elastic member 40 at its desired position on sleeve 40 by confining elastic member 40 to the inner portions of seams 44 and 46 which are affixed to sleeve 20 by physical or chemical means. The degree of friction between finger 18 and sleeve 20 can be varied by increasing the constricting force of elastic member 40 or by increasing the area of sleeve 20 subject to the contstricting force of elastic member 40. Hence, a smaller diameter elastic member 40 could be used to increase the hold of sleeve 20 on a small finger inserted therein, or a wider elastic member 40 could be used to more evenly and effectively distribute a given constricting force to increase the area of increased friction.

Figure 5:
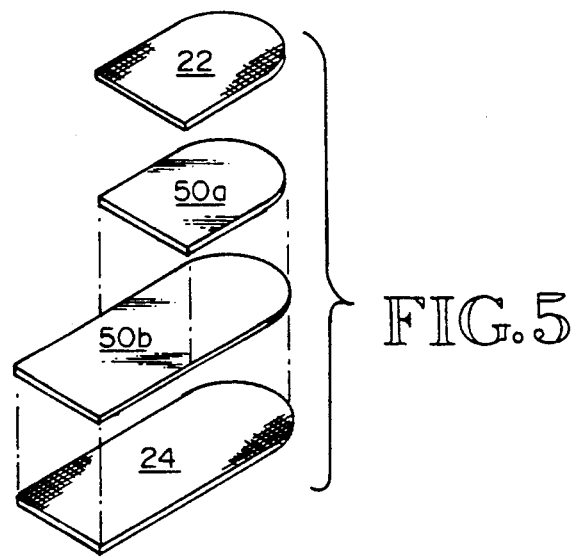
FIG. 5 is an exploded perspective view of the invention wherein two fluid impermeable layers are located intermediate the absorbent material and the skin of the finger.

An important feature of the invention provides for a fluid impermeable layer intermediate finger 18 and the absorbent surface of sleeve 20. By constructing sleeve 20 to have this fluid barrier, finger 18 will avoid contacting any fluid or debris absorbed or removed by sleeve 20. As illustrated in FIG. 5, fluid impermeable layer 50a is formed into the same shape as upper portion 22 and fluid impermeable layer 50b is formed into the same shape as lower portion 24, and is incorporated into the manufacturing process just prior to joining the upper portion 22 and lower portion 24. Those persons skilled in the art will realize that numerous means exist to provide such a fluid barrier. Similar means include, but are not limited to, gauze having such a barrier preformed on one side, a fluid absorbent material impregnated with a fluid impermeable substance, bonding a thermoplastic sheet to a fluid absorbing surface, etc. As discussed previously, the many benefits of providing a fluid impervious layer between finger 18 and fluids and debris collected by fluid impervious sleeve 20' include reduced risk of contact with detrimental bacteria and viruses, reduced contamination of substances and compounds from a finger 18 to the area being explored, and simple cleanliness. Thus, nearly all of the advantages associated with using a full hand glove when performing similar tasks can be found when using sleeve 20'.

From the foregoing, it also should be clear that the incorporation of appendage 30 further reduces the chances of skin contact with fluids and debris collected during use of sleeve 20'—appendage 30 is not usually exposed to the probed environment and therefore is not contaminated by the fluids and debris or cause contamination of the cleaned area. Thus, removal of sleeve 20' by grasping appendage 30 decreases the risk of exposing the grasping fingers to the collected fluid, and application of sleeve 20' to a finger 18 by holding on to appendage 30 decreases the risk of contaminating the absorbent and sterile surface of sleeve 20'.

When incorporating appendage 30 and one or more fluid impermeable layers, sleeve 20' is especially adapted to receive medication or an antiseptic, although these features would not be necesssary for this type of use. In practice, each sleeve 20' would be treated with a desired substance prior to packaging. The packaging would keep sleeve 20' isolated from the external environment. Upon open the packaging, sleeve 20 would be ready for immediate use as a cleaner, disinfectant applicator, or medication applicator.

From the foregoing, it can be seen that the invention has a variety of uses: in the fields of dentistry, medicine, cosmetics, etc. Therefore, the invention is to be judged not by the foregoing description but by the appended claims, properly interpreted in light of current judicial standards.

What is claimed is:

1. An appliance for absorbing and removing particles and fluid from confined body cavities and canals comprising:
    a sleeve having an absorbent material formed to fit over a human finger wherein the sleeve has an exterior surface and an interior surface defining a collapsible void, and wherein the interior surface substantially surrounds at least the distal phalanx of the finger when inserted into the collapsible void; and
    an annular elastic band located at the outer circumference of the sleeve and held thereto by a similarly shaped sheet of material which is attached at the outer surface of the sleeve, the combination provided to enhance the friction between the sleeve and a finger inserted in the void.

2. The appliance of claim 1 wherein a palmer portion of the sleeve is axially longer than a dorsal portion of the sleeve.

3. The appliance of claim 2 further comprising an appendage attached to a proximal portion of the palmer portion of the sleeve to facilitate application and removal of the sleeve from the finger.

4. The appliance of claim 1 further comprising an appendage attached to a proximal portion of the palmer portion of the sleeve to facilitate application and removal of the sleeve from the finger.

5. The appliance of claim 1 further comprising a fluid impermeable layer located intermediate the exterior surface of the absorbent material and an inserted finger wherein the layer is fixedly attached to the sleeve.

6. The appliance of claim 1 wherein the absorbent material has been exposed to a disinfecting substance during a manufacturing process.

7. The appliance of claim 1 wherein the absorbent material has been exposed to an antibiotic substance during a manufacturing process.

* * * * *